United States Patent
Baker et al.

(10) Patent No.: US 6,638,966 B2
(45) Date of Patent: *Oct. 28, 2003

(54) USE OF MELATONIN ANALOGUES FOR INDUCTION OF GENERAL ANESTHESIA

(75) Inventors: Max T. Baker, Iowa City, IA (US); Mohamed Naguib Attala, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/078,643

(22) Filed: Feb. 19, 2002

(65) Prior Publication Data

US 2002/0120002 A1 Aug. 29, 2002

Related U.S. Application Data

(63) Continuation-in-part of application No. 09/927,687, filed on Aug. 10, 2001, now Pat. No. 6,552,064.
(60) Provisional application No. 60/233,785, filed on Sep. 19, 2000.

(51) Int. Cl.[7] ............................................. A61K 31/40
(52) U.S. Cl. ....................... 514/419; 514/415; 514/816; 514/817; 514/818
(58) Field of Search ................................ 514/419, 415, 514/816, 817, 818

(56) References Cited

U.S. PATENT DOCUMENTS 5,196,435 A * 3/1993 Clemens et al. ............ 514/284
6,004,991 A * 12/1999 Fourtillan et al. .......... 514/415
6,071,928 A    6/2000 Curtis et al.

FOREIGN PATENT DOCUMENTS

EP    0 513 702 A2    11/1992
EP    0 867 181 A1    9/1998

OTHER PUBLICATIONS

CA111:153621, Dubocovich et al., WO 8901472, 2/23/1989, abstract.*

Mallo et al., Acto Endocrinology, 1988 Dec., 199(4), 474–80, abstract.*

Vijayalaxmi et al., "Melatonin and protection from whole–body irradiation: survival studies in mice.", *Mutation Research*, Netherlands Mar. 10, 1999, vol. 425, No. 1, (Mar. 10, 1999), pp. 21–27, XP002222723, ISSN: 0027–5107, abstract.

Chaiyakul, "Melatonin Dose–Dependently Inhibits Ketamine–induced Anesthesia in Rats", *Society for Neuroscience Abstracts*, vol. 25, No. 1–2, 1999, p. 922 XP001109176, 19th Annual Meeting of the Society for Neuroscience; Miami Beach, Florida, USA; Oct. 23–28–1999, ISSN: 0190–5295, abstract.

* cited by examiner

*Primary Examiner*—Rebecca Cook
(74) *Attorney, Agent, or Firm*—McKee, Voorhees & Sease, P.L.C.

(57) ABSTRACT

Melatonin (N-acetyl-5-methoxytryptamine), or its biologically active analogues, are used to induce anesthesia.

29 Claims, No Drawings

USE OF MELATONIN ANALOGUES FOR INDUCTION OF GENERAL ANESTHESIA

CROSS REFERENCE TO RELATED APPLICATIONS

This application is a continuation-in-part of Ser. No. 09/927,687 filed Aug. 10, 2001, now U.S. Pat. No. 6,552,064 which itself is a continuation-in-part of Serial No. 60/233,785 filed Sep. 19, 2000, and this case claims the benefit of those earlier filing dates.

BACKGROUND OF THE INVENTION

In the medical field there is a continuing need for new compounds having demonstrated use for inducing anesthesia. It is not only important to induce beneficial anesthesia, but it must be done in a manner that limits toxicity to patients, and as well, minimizes what is known as "anesthesia hangover".

The pineal hormone melatonin (N-acetyl-5-c) has several putative functions, including regulation of circadian rhythms, regulation of the reproductive axis and antioxidant activity. Autoradiographic studies and receptor assays have demonstrated the presence of melatonin receptors in various regions of the central nervous system and in other tissues in humans.

Exogenous administration of melatonin has been found by several investigators to facilitate sleep onset and improve quality of sleep. Available data suggest that the sleep-inducing properties of melatonin may differ from those of benzodiazepines. Benzodiazepines decrease duration of REM sleep after single administration of a high dose or long-term administration of low dose. Benzodiazepines also reduce slow-wave sleep, thus negatively influencing sleep quality. In contrast, a single low dose of melatonin produced no suppression of REM sleep. Furthermore, unlike benzodiazepines, melatonin does not induce "hangover" effects.

In a previous publication of one of the inventors, *British Journal of Anesthesia* 82(6):875–80(1999), low-level dosing of oral melatonin in a sublingual fashion was demonstrated as an effective pre-medication, prior to administering a general anesthetic. Patients who were administered such low-level doses sublingually had a significant decrease in anxiety levels and an increase in levels of sedation before operation. However, as pointed out in that article, the use of melatonin in anesthesia had as of then never been evaluated properly, and to the inventor's present knowledge it has never been used as a general anesthetic prior to this series of applications.

The invention of Ser. No. 09/927,687 had as its primary objective the development of pineal hormone melatonin (N-acetyl-5-methoxytryptamine) or its biologically active analogues as a general anesthetic which can be used without any significant anesthetic hangover. The continuing need in the art for meeting that objective was readily apparent.

With reference to the continuing need referred to above, applicants have continued to work with melatonin and its analogues to derive improved compounds which may be used for anesthetic effect generally and in small doses for hypnotic effect sedation or even sleep inducement. This continuing work has evolved into the discovery that 2-trihalo methyl melatonins and in particular the 2-trifluoromethylmelatonin are substantially more active in anesthetic effect than melatonin itself. The result of this increased activity means that the compounds may be used in larger doses for general anesthesia, but in smaller doses for hypnotic effect and sedation and sleep effect.

Further discoveries since the filing of the original application have revealed a particularly effective pharmaceutical carrier for melatonin, melatonin analogues and the improved derivatives of the present invention. The carrier allows dissolving and high concentrations of melatonin or its analogues. The preferred carrier is comprised of one volume of 1-methyl-2-pyrrolidinone, one volume of propylene glycol and two volumes of water. It goes without saying that the volumetric ratios of these carrier solvents may be varied somewhat, depending upon the circumstances.

SUMMARY OF THE INVENTION

Anesthetic compositions are prepared using a pharmaceutically-acceptable carrier, preferably a preferred carrier comprising a mixture of one volume of 1-methyl-2-pyrrolidinone, one volume of propylene glycol and two volumes of water and an anesthetic-inducing effective amount of melatonin or biologically active analogues of melatonin such as 2-trifluoromethylmelatonin. The invention also relates to the method of administration using the described compositions.

DETAILED DESCRIPTION OF THE PREFERRED EMBODIMENT

N-acetyl-5-methoxytryptamine (melatonin) is synthesized mainly by the pineal gland, and to a lesser extent by extra pineal tissues such as the retina, harderian gland, and gastrointestinal tract. Melatonin has the following structure:

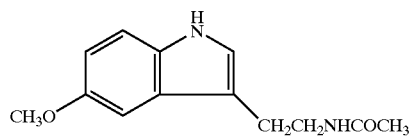

As seen, the chemical formula for melatonin is N-acetyl-5-methoxytryptamine. From time to time in the specification applicant uses the term "N-acetyl-5-methoxytryptamine (melatonin), or its biologically active analogues". As used herein, this phrase refers to the precise compound itself and other compounds having the same general structure, but only differing in minor moieties, and therefore still having the same biological activity of anesthetic-inducing effectiveness. The biologically active compound of the present invention, such as melatonin, may be derived or extracted from the pineal gland, or it can be synthesized from 5-Methoxyindol as a starting material by known routes, Szmuszkovicz et al., *J. Org. Chem.* 25, 857 (1960). Biochemical role of melatonin: *Chem. & Eng. News* 45, 40 (May 1, 1967).

The analogue of the present invention that has been found to be more active than melatonin itself, and therefore can be used in smaller dosage levels and even at such small dosage levels to effectively induce hypnotic state, sedation or sleep, is 2-trifluoromethylmelatonin. As can be seen from a comparison with the formula for melatonin it contains a carbon trifluoromethyl moiety at the 2-position, replacing a hydrogen moiety from melatonin. While 2-trifluoromethylmelatonin is the most effective so far found to date, it may be that other 2-position moieties such as 2-trihalo moieties in general can be used. Therefore, within the term 2-trihalo we intend to encompass chloride, fluoride, bromide and iodide.

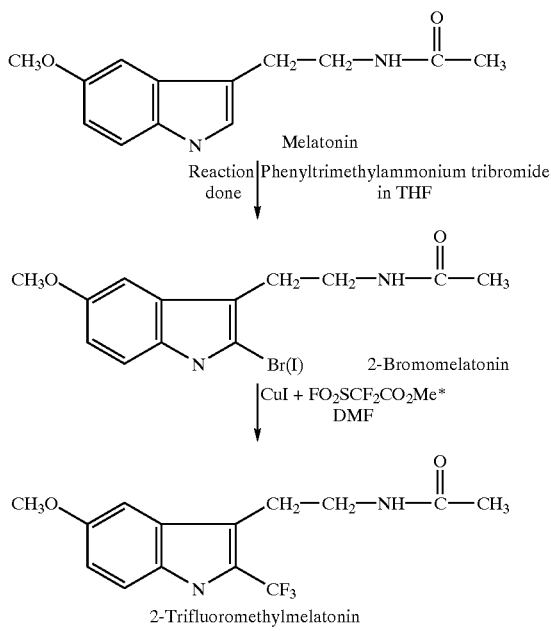

2-Trifluoromethylmelatonin

The anesthetic active, i.e., the N-acetyl-5-methoxytryptamine (melatonin), or its biologically active analogues, can be administered with traditionally acceptable pharmaceutical carriers as described in the patent applications. Examples include Intralipid®, Cyclodextrin, and others, some of which are briefly hereinafter described. However, there is no need for detailed description of suitable anesthetic carriers because they are so well known in the industry. Here, however, the present applicants have discovered a preferred pharmaceutical carrier system.

Melatonin has previously been administered to animals in organic solvents that have central nervous system (CNS) effects. Such organic solvents frequently consist of ethanol in water. An administration vehicle not having CNS effects is desired for the administration of melatonin to achieve pure melatonin effects.

It was discovered that melatonin could be dissolved in high concentrations in a solvent comprised of 1 volume 1-methyl-2-pyrrolidinone, 1 volume propylene glycol and 2 volumes of water. Melatonin can be dissolved up to a concentration of 300 mg/ml in this solvent. The volume ratios here expressed are preferred but generally can be within the range of 25% or less by volume of 1-methyl-2-pyrrolidinone.

Intravenous administration of melatonin in this solvent system results in a rapid increase in blood melatonin concentrations in rats that are suitable to cause an unexpected anesthetic effect without causing toxic side effects.

Formulations containing melatonin analogues that consist of melatonin or its analogues and 1-methyl-2-pyrrolidinone in water can be used or formulations containing melatonin analogues and 1-methyl-2-pyrrolidinone combined with water and other known inert solvents such as propylene glycol, polypropylglycol, polysorbitans and cyclodextrins can be used.

Derivatives or analogues of melatonin, such as 2-bromomelatonin and 2-phenylmelatonin may be administered in solvents described above containing 1-methyl-2-pyrrolidinone for delivery to mammals.

As earlier expressed, 1-methyl-2-pyrrolidinone may be present in the disclosed vehicles at concentrations less than 25% volume/volume. For example, concentrations of 1-methyl-pyrrolidinone may range from 5 to 25% or greater than 25% in water, or in water combined with propylene glycol, glycerol, dextrins and/or polysorbitans.

The composition may be administered by conventional administration methods for anesthetics, i.e., oral administration, nasal respiratory administration, bolus injection, intravenous administration by repeated doses or by continuous infusion, rectal, vaginal, sublingual, cutaneous and slow release routes. It may be, and often is preferred, that it be administered in two or more ways, such as by bolus injection followed by continuous intravenous administration.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a melatonin biologically active analogue as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition, or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, particularly 0.1 and 0.5 μm, and have a pH in the range of 5.5 to 8.0.

Particularly preferred emulsion compositions are those prepared by mixing an active compound with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device, or the nebulising device may be attached to a face mask, tent or intermittent positive pressure breathing machine. Solution, suspension or powder compositions may be administered, preferably orally or nasally, from devices which deliver the formulation in an appropriate manner.

The anesthetic may be used alone or often in combination with other anesthetics simultaneously administered. Put another way, it will be appreciated that when using any combination described herein, both the compound of melatonin or its analogue and the other active agent(s) can be administered to a patient, within a reasonable period of time. It may indeed act synergistically with other anesthetic drugs. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active compound may be administered as a tablet and then, within a reasonable period of time, the second active component may be administered either as an oral dosage form such as a tablet or a fast-dissolving oral dosage form. By a "fast dissolving oral formulation" is meant, an oral delivery form which, when placed on the tongue of a patient, dissolves within about 10 seconds.

The dosage will vary depending upon the deepness of the anesthesia desired, but based upon limited studies to date, it is believed that the dosage most effective will be within the range of 0.001 mg/kg of body weight to about 500 mg/kg of body weight, more predictably preferred is the range of 5 mg/kg of body weight to about 350 mg/kg of body weight.

The synthesis of 2-trifluoromethylmelatonin may be summarized by the following reaction scheme.

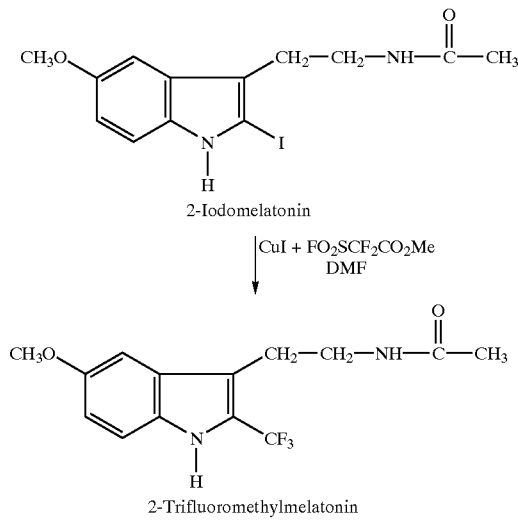

2-Trifluoromethylmelatonin

In word description, the reaction synthesis of 2-trifluoromethylmelatonin can be described as follows. 2-Iodomelatonin (1 g, FW=232) was dissolved in 20 ml DMF in a round bottom glass reaction flask fitted with a condenser. CuI (1.3 g, FW=190) and methyl 2,2-difluoro-2-(fluorosulfonyl)acetate, 1.2 g, (FW=192) was added and the reaction mixture heated to 60–80° C. at least 3 hr.

Following the reaction period, the reaction mixture was chilled on ice and DMF removed from the mixture by rotatory evaporation. 15 ml water was added and the reaction mixture neutralized. Melatonin products were extracted from the aqueous phase with methylene chloride (20 ml×2). The products of the reaction were analyzed by GC/MS and found to contain a fraction that corresponds to trifluoromethylmelatonin (M$^+$, m/z 300).

Trifluoromethylmelatonin analysis was performed by silica gel TLC (Silica Gel 60, Fisher Scientific, Inc.) using anhydrous ethyl acetate as mobile phase. Bands were detected by fluorescence (366 nm). Isolation of one band yielded pure trifluoromethylmelatonin. Recovery and weighing of the fraction demonstrates a yield of greater than 25–30%. 2-Trifluoromethylmelatonin was confirmed by proton and fluorine NMR. When patients are administered N-acetyl-5-methoxytryptamine (melatonin) or its biologically active analogues, there is a noticeable decrease in anesthetic hangover. It is believed that this occurs because melatonin itself is a naturally-occurring hormone synthesized in the body by the pineal gland.

The following anesthetic examples are offered to further illustrate, but not limit the invention disclosed herein.

EXAMPLES

All experiments were carried out in male Sprague-Dawley rats (300–350 g). Rats were maintained on a 12 hour light/12 hour dark cycle with free access to food and water. All surgical procedures were performed under sterile conditions (skin preparation, sterile filed drape, gloves, mask, etc.). All instruments and materials were ethylene oxide sterilized. Non-fasting adult male Sprague Dawley rats (~300 gm) were anesthetized with halothane in oxygen and weighed. The hair over the ventral neck and over the back (between the scapulae) was removed with an electric razor. In the supine position the ventral neck was washed with povidone-iodine, followed by a 3-cm skin incision, just left of midline. All bleeding points were cauterized. Both the left jugular vein and left common carotid artery were isolated via blunt dissection. The left jugular vein was cannulated with a heparinized (20 U/ml) saline-filled silastic catheter (0.012-in ID, 0.025-in OD) advanced ~3-cm into the right atrium. The jugular catheter was secured to the vein with 4-0 silk at the point of insertion, as well as at the rostral jugular ligature.

After implantation of intravascular catheters, rats were housed in individual stainless steel cages. Studies with melatonin were carried out 5–7 days after surgery. Crystalline Melatonin powder was obtained from Sigma (Sigma Chemical Co. St. Louis, Mo.).

The melatonin was prepared for anesthetic use in the following manner:
100 mg melatonin added to 1 ml of intralipid and 1 ml of Ringer's Lactate (final concentration=50 mg melatonin/ml).

Results
Rat 1: 250 mg/kg followed approximately 1 minute later by 65 mg/kg: the animal was very drugged but did not lose righting reflex.
Rat 2: 250 mg/kg resulted in loss of righting and eyelash reflexes and inability to pull his hind paw in response to pressure applied to it.
Rat 3: 320 mg/kg resulted in loss of righting and eyelash reflexes and inability to pull his hind paw in response to pressure applied to it.
Rat 4: 370 mg/kg resulted in loss of righting and eyelash reflexes and inability to pull his hind paw in response to pressure applied to it.

Additional preparation of melatonin occurred with cyclodextrin as follows:
100 mg melatonin added to 1 ml of cyclodextrin 40% and 1 ml of intralipid (final concentration=50 mg melatonin/ml)
Results
Rat 1: 315 mg/kg: the animal moves slowly but no loss of righting reflex.
Rat 2: 460 mg/kg resulted in loss of righting reflex.
Another group of rats received the solvent alone and did not result in any effect. This demonstrates the anesthetic property of melatonin, and that the invention accomplishes its stated objectives.
Melatonin in 40% Cyclodextrin
Rat 1: 315 mg/kg resulted in ptosis, loss of eye blink response and loss of paw pinch response to a pressure of 60 mmHg using a very low profile load cell (Omega part number LCKD-1KG, measurement range of 0–1 kg) from OMEGA Engineering, INC. One Omega Drive, Stamford, Conn. 06907-0047. The righting reflex was lost for 27 min.
Rat 2: 374 mg/kg resulted in ptosis and loss of eye blink response. The righting reflex was lost for 15 min. The animal responded to a paw pinch response to a pressure of 60 mmHg by pulling his paw without vocalization.
Rat 3: Administration of the solvent (40% cyclodextrin) did not affect the animal behavior and did not result in sedation or hypnosis.

In a recent publication of the inventor concerning this invention, additional data relating to the invention is disclosed, *Anesthesia and Analgesia*, 91:473–479(2000), the disclosure of which is incorporated herein by reference.

The following examples are comparative examples demonstrating the effectiveness of melatonin for induction of general anesthesia in rats and how it compares to other known anesthetics in inducing general anesthesia.

COMPARATIVE EXAMPLES

The goal of these examples was to determine the doses of melatonin, thiopental and propofol needed to induce anesthesia in 50% and 95% of rats and to evaluate the time course of different indices of anesthesia. Rats were randomly assigned to receive three cumulative doses of 6.67 mg/kg i.v. thiopental, 3.3 mg/kg i.v. propofol or 70 mg/kg i.v. melatonin or three cumulative injections of the vehicle in which these drugs were dissolved at intervals of approximately 1 min. After the final cumulative dose, measurements of anesthesia end-points were made at fixed intervals for an additional 20 minutes. Separate groups of rats received a single bolus injection of 20 mg/kg i.v. thiopental, 10 mg/kg i.v. propofol or 275 mg/kg i.v. of melatonin or the vehicle in which these drugs were dissolved. Measurements of anesthesia end-points were made in these rats at fixed intervals for 20 minutes. Righting reflex was scored on a four-point scale (1=immediate/brisk, both feet under the rat; 2=complete, but slower than normal; 3=slow, feet not placed under body; and 4=absent). The threshold pressure (mm Hg) at which the rat withdrew or vocalized after pinch of one hindpaw was measured. For paw pinch, a subminiature, very low profile load cell Omega part number LCKD-1KG, measurement range of 0–1 kg) (OMEGA Engineering, INC., Stamford, Conn.) was used to measure the amount of pressure applied to the rat's paw. The action of compressing the load cell between the faces of the sponge clamp assembly results in a change in impedance within the load cell, and this in turn, was then converted to mm Hg pressure by the monitor. The presence or absence of eyelash reflex was noted on a three-point scale (1=normal, 2=weak; and 3=absent). The strength of grip by the forepaws was determined on a four-point scale (0=absent, 1=weak, 2=moderate and 3=strong).

Thiopental was purchased from Abbott Laboratories (Northern Chicago, Ill.). Propofol was purchased from Zeneca Pharmaceuticals (Wilmington, Del.). Melatonin was purchased from Sigma Chemical Co. (St. Louis, Mo.). Thiopental and propofol were dissolved in saline and Intralipid™ respectively. Melatonin was dissolved in a mixture comprising 25% v/v propylene glycol and 25% v/v 1-methyl-2-pyrrolidinone in sterile water. For the cumulative injections, the individual doses were administered in a volume of 0.2 ml and the maximum volume of drug injected did not exceed 0.6 ml. For the bolus injections, the volume of drug injected ranged from 0.6 to 0.75 ml.

Intravenous injection of saline, Intralipid™ or the vehicle for melatonin did not affect righting reflex, grip strength, or eyelash reflex. Neither saline nor Intralipid™ altered paw withdrawal threshold. However, the vehicle for melatonin produced a significant short-lived increase in paw withdrawal threshold that subsequently decreased to near baseline levels.

Cumulative i.v. injection of divided doses of thiopental caused a progressive loss of righting reflex, grip strength and eyelash reflex with an estimated $ED_{95}$ (and 95% CI) for the loss of righting reflex of 23.8 (15.4–36.7) mg/kg i.v. Bolus injection of 20 mg/kg thiopental resulted in an immediate loss of righting reflex and grip strength that was maximal at 1 min and resolved within 15 min. These effects were not accompanied by a change in paw withdrawal threshold.

Cumulative i.v. injection of divided doses of propofol caused a progressive loss of righting reflex, grip strength and eyelash reflex with an estimated $ED_{95}$ (and 95% CI) for loss of righting reflex of 14.9 (6.4–34.9) mg/kg. Bolus injection of 10 mg/kg i.v. propofol caused an immediate loss of righting reflex and grip strength that was maximal for 5 min and resolved within 10 min. These effects were accomplished by a significant increase in paw withdrawal threshold of similar duration.

Cumulative i.v. injection of divided doses of melatonin caused a progressive loss of righting reflex and grip strength, but did not appreciably blunt the eyelash reflex. It also dose-dependently increased paw withdrawal threshold. The estimated $ED_{95}$ (and 95% CI) of melatonin for loss of righting reflex was 312 (205–476) mg/kg i.v. Bolus injection of 275 mg/kg i.v. melatonin resulted in an immediate loss of righting reflex and grip strength that was maximal for 5 min and resolved to near baseline values by 15 min. This dose of melatonin also increased paw withdrawal threshold as compared to vehicle. The increase in paw withdrawal threshold persisted for at least 20 min, and was apparent at doses of 140 mg/kg or greater.

This data demonstrates that intravenous administration of melatonin or its analogues can induce general anesthesia. This anesthesia is accompanied by an analgesia that persists after the return of consciousness.

What is claimed is:

1. An anesthetic composition comprising:
   a pharmaceutically acceptable anesthetic carrier, and an anesthetic inducing effective amount of a 2-trihalomethylmelatonin.

2. The composition of claim 1 wherein the halo moiety in 2-trihalomethylmelatonin is selected from the group consisting of chloride, fluoride, bromide, iodide and combinations thereof.

3. The composition of claim 2 wherein the 2-trihalomethylmelatonin is 2-trifluoromethylmelatonin.

4. The anesthetic composition of claim 1 wherein the amount of 2-trihalomethylmelatonin is sufficient to provide a dose of from about 0.001 mg/kg of body weight to about 500 mg/kg of body weight.

5. The anesthetic composition of claim 1 wherein the amount of 2-trihalomethylmelatonin is sufficient to provide a dose of from about 5 mg/kg of body weight to about 350 mg/kg of body weight.

6. A method of inducing sedative effect as well as general anesthesia, comprising:

administering to a mammal an effective amount of 2-trihalomethylmelatonin.

7. The method of claim 6 wherein the active anesthetic is 2-trifluoromethylmelatonin.

8. The method of claim 6 wherein the amount of 2-trihalomethylmelatonin administered is a dose of from about 0.001 mg/kg of body weight to about 500 mg/kg of body weight.

9. The method of claim 6 wherein the amount of 2-trihalomethylmelatonin administered is from about 5 mg/kg of body weight to about 350 mg/kg of body weight.

10. The method of claim 6 wherein the administering is by a method selected from the group consisting of oral administration, nasal respiratory administration, bolus injection, intravenous administration, continuing infusion, rectal, vaginal, sublingual and cutaneous administration.

11. The method of claim 10 wherein the administration is by an initial bolus injection, followed by intravenous administration.

12. The method of claim 6 wherein the administration is in combination with simultaneous administration of another anesthetic.

13. The method of claim 6 wherein the 2-trihalomethylmelatonin is derived from melatonin which is secreted from the pineal gland.

14. An anesthetic composition comprising:

a pharmaceutically acceptable carrier which is a mixed solvent of 1-methyl-2-pyrrolidinone, propylene glycol and water, and an anesthetic inducing effective amount of 2-trihalomethylmelatonin.

15. An anesthetic composition of claim 14 wherein the carrier is 1 volume part of 1-methyl-2-pyrrolidinone, 1 volume part of propylene glycol and 2 volume parts of water.

16. The anesthetic composition of claim 14, wherein the anesthetic carrier is water mixed with an anesthetic carrier selected from the group consisting of 1-methyl-2-pyrrolidinone, propylene glycol, polypropylglycol, polysorbitans and cyclodextrins.

17. An anesthetic composition comprising:

a pharmaceutically acceptable anesthetic carrier, and an anesthetic inducing effective amount of 2-phenylmelatonin.

18. The anesthetic composition of claim 17 wherein the amount of compound is sufficient to provide a dose of from about 0.001 mg/kg of body weight to about 500 mg/kg of body weight.

19. The anesthetic composition of claim 17 wherein the amount of compound is sufficient to provide a dose from about 5 mg/kg of body weight to about 350 mg/kg of body weight.

20. A method of inducing general anesthesia, comprising:

administering to a mammal an effective amount of a compound selected from the group consisting of 2-bromomelatonin and 2-phenylmelatonin.

21. The method of claim 20 wherein the amount of a compound administered is a dose of from about 0.001 mg/kg of body weight to about 500 mg/kg of body weight.

22. The method of claim 20 wherein the amount of a compound administered is a dose from about 5 mg/kg of body weight to about 350 mg/kg of body weight.

23. An anesthetic composition comprising:

a pharmaceutically acceptable carrier which is a mixed solvent of 1-methyl-2-pyrrolidinone, propylene glycol and water and an anesthetic inducing effective amount of 2-phenylmelatonin.

24. The anesthetic composition of claim 23 wherein the carrier is 1 volume part of 1-methyl-2-pyrrolidinone, 1 volume part of propylene glycol and 2 volume parts of water.

25. The anesthetic composition of claim 24 wherein the anesthetic carrier is water mixed with an anesthetic carrier selected from the group consisting of 1-methyl-2-pyrrolidinone, propylene glycol, polypropylglycol, polysorbitans and cyclodextrins.

26. The method of claim 20 wherein the compound is derived from melatonin which is secreted from the pineal gland.

27. The method of claim 20 wherein the administering is by a method selected from the group consisting of oral administration, nasal respiratory administration, bolus injection, intravenous administration, continuing infusion, rectal, vaginal, sublingual and cutaneous administration.

28. The method of claim 27 wherein the administration is by an initial bolus injection, followed by intravenous administration.

29. The method of claim 20 wherein the administration is in combination with simultaneous administration of another anesthetic.

* * * * *